(12) United States Patent
Cable et al.

(10) Patent No.: US 8,733,154 B2
(45) Date of Patent: *May 27, 2014

(54) LIQUID ANALYSIS USING CAPACITATIVE MICROMACHINED ULTRASOUND TRANSDUCERS

(71) Applicant: Matrix Sensors, Inc., Pleasanton, CA (US)

(72) Inventors: Michael D. Cable, Danville, CA (US); Matthias Steiert, Albany, CA (US)

(73) Assignee: Matrix Sensors, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/851,834

(22) Filed: Mar. 27, 2013

(65) Prior Publication Data

US 2013/0205878 A1 Aug. 15, 2013

Related U.S. Application Data

(63) Continuation of application No. 12/686,916, filed on Jan. 13, 2010, now Pat. No. 8,424,370.

(60) Provisional application No. 61/145,437, filed on Jan. 16, 2009.

(51) Int. Cl.
*G01N 29/24* (2006.01)

(52) U.S. Cl.
USPC ........................................................ 73/64.53

(58) Field of Classification Search
USPC ........................................................ 73/64.53
See application file for complete search history.

(56) References Cited

U.S. PATENT DOCUMENTS

| 4,242,096 | A  | * | 12/1980 | Oliveira et al. ............... 436/500 |
| 5,550,063 | A  | * | 8/1996  | Bogart ........................... 436/518 |
| 5,892,144 | A  | * | 4/1999  | Meller et al. ................. 73/64.42 |
| 6,464,848 | B1 | * | 10/2002 | Matsumoto ............. 204/403.06 |
| 6,854,338 | B2 | * | 2/2005  | Khuri-Yakub et al. .... 73/861.27 |
| 7,051,574 | B2 |   | 5/2006  | Peck |
| 7,305,883 | B2 |   | 12/2007 | Khuri-Yakub et al. |
| 7,350,403 | B2 | * | 4/2008  | Yakhno et al. ............... 73/64.53 |
| 7,361,821 | B2 |   | 4/2008  | Chan et al. |
| 7,458,271 | B2 | * | 12/2008 | Mutz ............................... 73/727 |
| 7,691,583 | B2 | * | 4/2010  | Craighead et al. ............. 435/7.1 |

(Continued)

FOREIGN PATENT DOCUMENTS

WO  WO 2004/036207  4/2004

OTHER PUBLICATIONS

International Search Report dated Mar. 19, 2010 in PCT Application No. PCT/US2010/021034.

(Continued)

*Primary Examiner* — John Fitzgerald
(74) *Attorney, Agent, or Firm* — Beyer Law Group LLP (57) ABSTRACT

A method for analyzing liquid samples may comprise applying a liquid to a cMUT device having a plurality of sensors, drying the plurality of sensors, electronically detecting an agent bound to each of the plurality of sensors, wherein the electrical circuit provides a sensor output responsive to a mechanical resonance frequency of the sensor, wherein the mechanical resonance frequency of the sensor is responsive to the binding of an agent to the functionalized membrane, and determining the mass of the agent bound to each of the plurality of sensors.

6 Claims, 8 Drawing Sheets

(56) References Cited

U.S. PATENT DOCUMENTS

| | | | |
|---|---|---|---|
| 7,721,590 B2* | 5/2010 | Kolosov et al. | 73/54.41 |
| 7,900,521 B2* | 3/2011 | Hooper et al. | 73/756 |
| 7,939,273 B2* | 5/2011 | Craighead et al. | 435/7.1 |
| 8,424,370 B2* | 4/2013 | Cable et al. | 73/64.53 |
| 2002/0048531 A1 | 4/2002 | Fonash et al. | |
| 2003/0113766 A1* | 6/2003 | Pepper et al. | 435/6 |
| 2004/0129064 A1 | 7/2004 | Hinterdorfer et al. | |
| 2004/0216515 A1* | 11/2004 | Yakhno et al. | 73/64.53 |
| 2004/0236223 A1* | 11/2004 | Barnes et al. | 600/459 |
| 2005/0241373 A1* | 11/2005 | Yakhno et al. | 73/61.45 |
| 2005/0262926 A1* | 12/2005 | Yakhno et al. | 73/64.53 |
| 2006/0223171 A1* | 10/2006 | Craighead et al. | 435/287.2 |
| 2007/0089516 A1* | 4/2007 | Khuri-Yakub et al. | 73/579 |
| 2008/0245135 A1 | 10/2008 | Aubin et al. | |
| 2010/0144059 A1* | 6/2010 | Frisk et al. | 436/518 |
| 2010/0199777 A1* | 8/2010 | Hooper et al. | 73/721 |

OTHER PUBLICATIONS

Written Opinion dated Mar. 19, 2010 in PCT Application No. PCT/US2010/021034.

* cited by examiner

LIQUID ANALYSIS USING CAPACITATIVE MICROMACHINED ULTRASOUND TRANSDUCERS

CROSS REFERENCE TO RELATED APPLICATIONS

This application is a continuation of U.S. patent application Ser. No. 12/686,916 filed on Jan. 13, 2010, now U.S. Pat. No. 8,424,370, which claims priority under 35 U.S.C. §119(e) to U.S. Provisional Patent Application No. 61/145,437, filed on Jan. 16, 2009, and entitled "LIQUID ANALYSIS USING CAPACITATIVE MICROMACHINED ULTRASOUND TRANSDUCERS," which is incorporated herein by reference in its entirety for all purposes.

FIELD OF THE INVENTION

The present disclosure relates generally to capacitative micromachined ultrasound transducers (cMUTs). More particularly, the present disclosure relates to the use of capacitative micromachined ultrasound transducers in liquid analysis.

BACKGROUND OF THE INVENTION

Resonant sensors depend on target molecules adsorbed in the sensing material to change properties that are reflected in the resonance frequency. A wide variety of cantilever, membrane and piezoelectric resonator-based sensors have been fabricated using MEMS technology. These sensors generally detect agents through the use of polymer films and coatings with selective adsorption for a specific agent or set of agents. Although these sensors provide a certain degree of sensitivity, it is desirable in many applications to have sensors with even higher sensitivities.

SUMMARY

Sensor technology using cMUTs may be used in liquid analysis. A method for analyzing liquid samples may comprise applying a liquid to a cMUT device having a plurality of sensors. Each of the plurality of sensors may have a) a functionalized membrane including a first electrode; b) a substrate including a second electrode, wherein the first and second electrodes define a capacitor; c) a support frame, wherein the support frame, the functionalized membrane, and the substrate define a vacuum gap; and d) an electrical circuit including the capacitor. Each of the plurality of sensors are dried and the agent bound to each of the plurality of sensors are detected, wherein the electrical circuit provides a sensor output responsive to a mechanical resonance frequency of the sensor, and wherein the mechanical resonance frequency of the sensor is responsive to the binding of an agent to the functionalized membrane. The mass of the agent bound to each of the plurality of sensors can then be determined.

These and other features will be presented in more detail in the following detailed description of the invention and the associated figures.

BRIEF DESCRIPTION OF THE DRAWINGS

The accompanying drawings, which are incorporated into and constitute a part of this specification, illustrate one or more example embodiments and, together with the description of example embodiments, serve to explain the principles and implementations.

In the drawings.

DETAILED DESCRIPTION

Embodiments are described herein in the context of liquid sampling analysis using capacitative micromachined ultrasound transducers (cMUTs). The following detailed description is illustrative only and is not intended to be in any way limiting. Other embodiments will readily suggest themselves to such skilled persons having the benefit of this disclosure. Reference will now be made in detail to implementations as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

A. cMUT Device Overview

A cMUT is a micromachined device having a substrate and a membrane supported above the substrate by an insulating material. A variable voltage applied between the substrate and membrane drives the membrane to vibrate and emit sound waves at ultrasonic frequencies. Arrays of cMUTs have been used for transmitting and receiving ultrasonic beam patterns in air and water over a frequency range from 10 kHz to 100 MHz. These cMUTs rely on the very large electric field (for example, $E>10^8$ V/m) in the gap of the capacitor to provide an electromechanical coupling coefficient close to unity.

cMUTs have been mostly used for medical imaging. In addition, they have been used to indirectly measure various fluid characteristics, based on processing of ultrasonic signals transmitted and received through the fluid. In current cMUT devices and applications, the cMUT devices are used to transmit and/or receive ultrasonic energy between the cMUT device and the environment. Moreover, to ensure reliable and consistent operation, cMUT membranes are normally designed to be non-reactive to chemicals, light, and other environmental factors that may alter or interfere with their operational characteristics. Due to their resonant character, cMUT devices have the potential to be used as sensors, in a manner similar to MEMS cantilever, membrane, and piezoelectric resonator-based sensors.

Figure 1A:
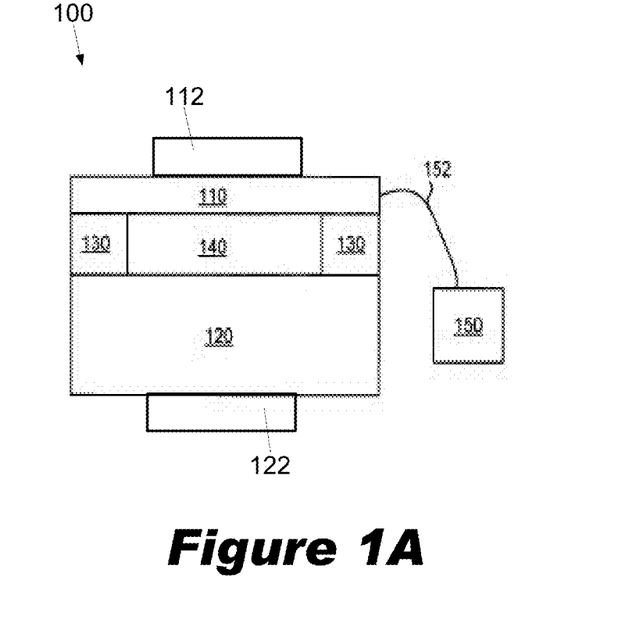
FIGS. 1A and 1B illustrate a schematic cross-sectional diagram of example sensors used in a capacitative micromachined ultrasound transducer.
Figure 1B:
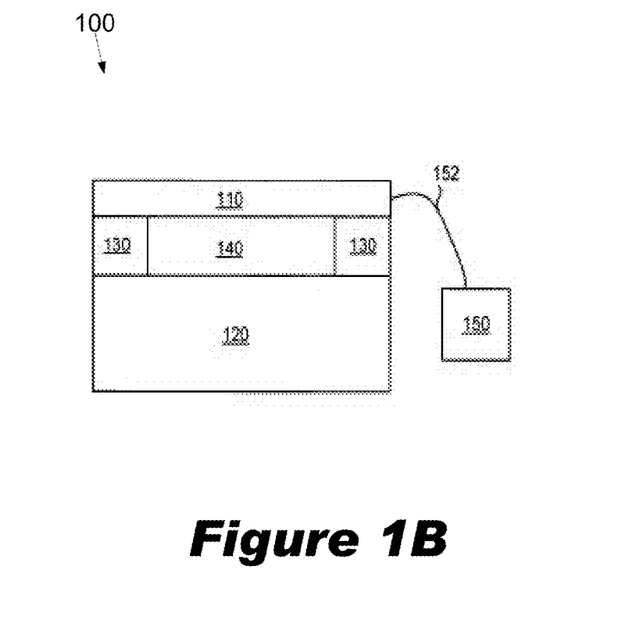

FIGS. 1A and 1B illustrate a schematic cross-sectional diagram of example sensors used in a capacitative micromachined ultrasound transducer. The cMUT or sensor 100 includes a functionalized membrane 110, which is supported over a substrate 120 by support frame 130. Functionalized membrane 110, support frame 130 and substrate 120 define a vacuum gap 140. Vacuum gap 140 may be between about 0.1 μm and about 5 μm in height. The cMUT or sensor 100 is connected to a detector 150 through connector 152. Detector 150 may be any type of detector that can detect the mechanical resonance frequency of functionalized membrane 110. Examples include, but are not limited to an optical detector, a mechanical stress detector, a magnetic detector, and a capacitance detector.

In one embodiment, functionalized membrane 110 is configured to be driven thermally (by applied heat or by thermal noise) or electrically, and an optical detector may be used to detect deflection or resonant frequency shifts of functionalized membrane 110. In other embodiments of the invention, functionalized membrane 110 may have thin piezoelectric or magnetic films that provide coupling. Resonant functionalized membranes 110 may be addressed by capacitor action or the change in the membrane deformation may be measured directly through the change in capacitance. Other detection modality to measure the change in the position of the membrane due to the attachment of agents to the film may be used.

Functionalized membrane 110 may operate, for example, at a mechanical resonance frequency of at least about 1 MHz. More specifically, between about 1 MHz and about 100 MHz. Also, the sensors have a Q factor of at least about 50.

The functionalized membrane 110 can contain a first electrode 112, and substrate 120 contains a second electrode 122. In this case, functionalized membrane 110 and substrate 120 are made of thin membranes that are essentially parallel plate capacitors with a gap between the plates. In one example, the conductive silicon wafer on which the functionalized membrane is fabricated, i.e. substrate 120, makes up one plate of the capacitor; a metal electrode 112 on top of the functionalized membrane 110 is the other plate of the capacitor. In one example, functionalized membrane 110, which is supported by insulating support frame 130, may be made of an insulating material, most commonly silicon nitride ($Si_3N_4$) and is coated with metal electrode 112. In another example, functionalized membrane 110 may be made of a highly conductive silicon. In this embodiment, there would be no need for first electrode 112 or second electrode 122 as illustrated in FIG. 1B. A low temperature oxide passivation layer may cover electrode 112 and functionalized membrane 110.

In one embodiment, functionalized membrane 110 may be constructed to have a large surface area. The surface area may be increased by adding additional cavities, as discussed below with reference to FIG. 4B. Each of the plurality of cavities may be formed with a specific dimension based upon the desired resonant frequency. Each of the plurality of cavities is then configured to communicate with a common electrode, which thereby forms a single sensor. This way, it is possible to attach many more molecules of a species to the membrane and increase the mass loading or induced stress, and hence improve sensitivity.

Figure 2:
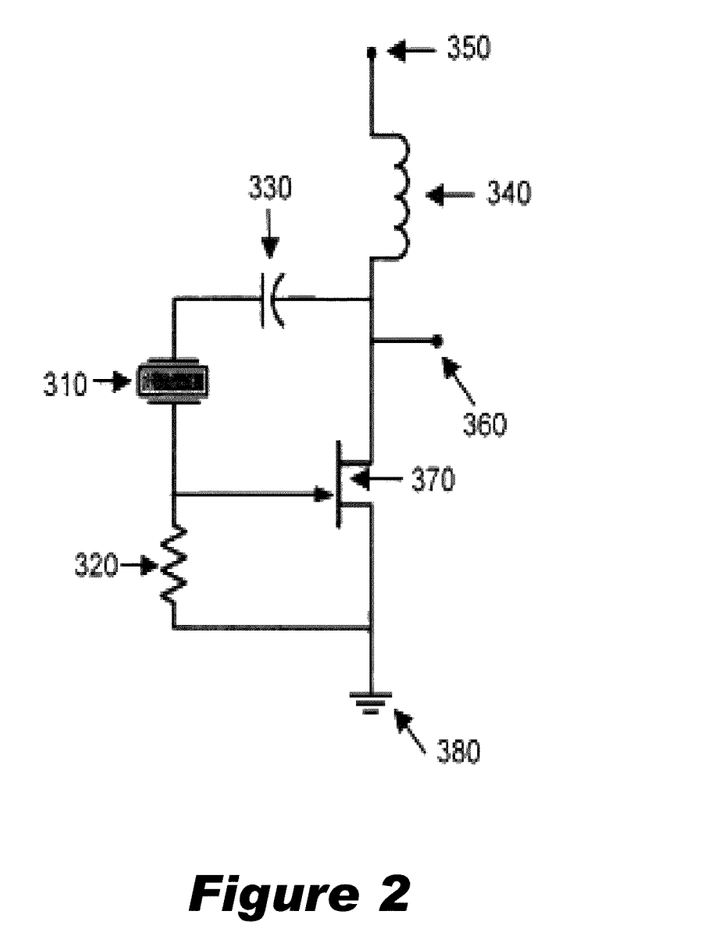
FIG. 2 illustrates an electrical circuit usable with the capacitative micromachined ultrasound transducer illustrated in FIG. 1.

FIG. 2 illustrates an example of an electrical circuit usable with the capacitative micromachined ultrasound transducer illustrated in FIG. 1. Such a circuit can be any of various circuits known in the art to establish a resonant circuit, such as a Pierce oscillator. The FIG. 2 circuit includes sensor 310, resistor 320, capacitor 330, inductor 340, DC voltage source 350, sensor output 360, transistor 370, and connection to ground 380. Many other circuits are available to establish a resonant circuit using the sensor's resonant electrical input impedance. The output of these circuits is, for example, a sinusoidal signal whose frequency is the measurable quantity of interest.

Generally, in use, the cMUT may be placed in the feedback loop of an amplifier and the gain of the amplifier adjusted such that the circuit oscillates. The frequency of the oscillator may be tuned by adjusting the DC bias that is applied to the cMUT. By controlling this DC bias the resonance or oscillation frequency is placed near the open circuit resonant frequency of the cMUT. This is done in order to reduce the noise in the oscillator circuit, and hence increase the sensitivity of the sensor. When something deposits on the membrane of the sensor, its open circuit resonance frequency shifts, and this imparts a frequency shift in the oscillator circuit. By measuring the resonant frequency of the oscillator, one can tell how much mass has deposited on the membrane. Other types of sensors that may be used are described, for example, in U.S. Pat. No. 7,305,883, entitled "Chemical Micromachined Microsensors", which is hereby incorporated by reference.

Figure 3:
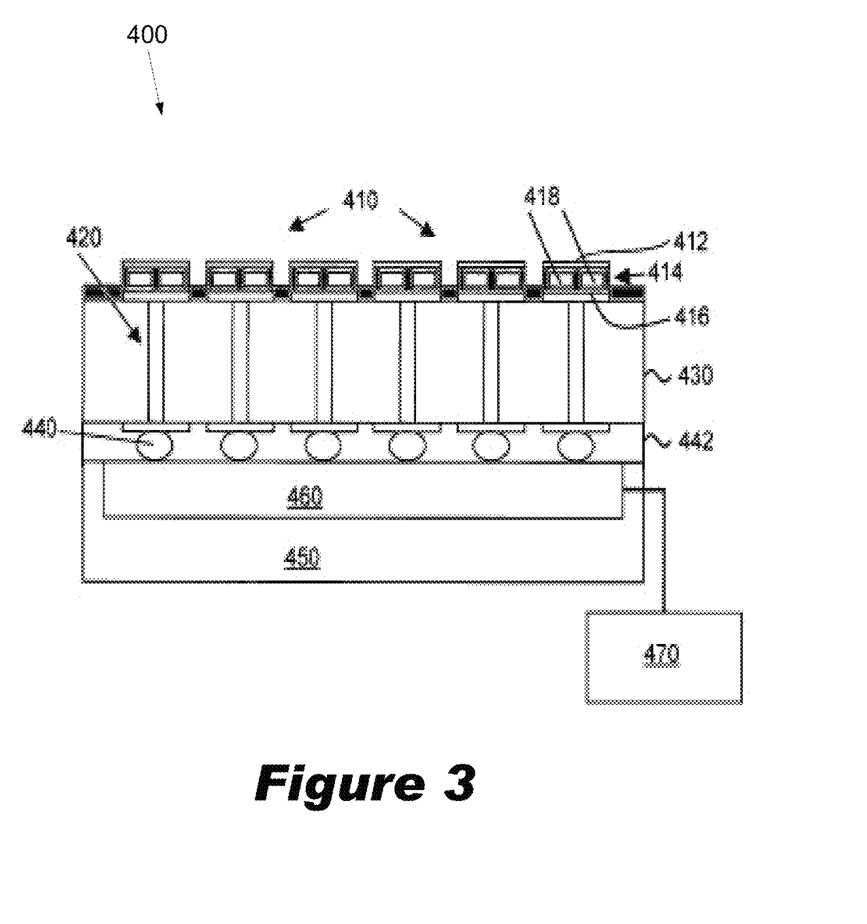
FIG. 3 illustrates a cross-sectional view of an array of capacitative micromachined ultrasound transducers.

FIG. 3 illustrates a cross-sectional view of an array of capacitative micromachined ultrasound transducers. In this example, each sensor 410 contains two cMUTs, each of which has a sensor membrane 412, support frame 414, substrate 416 and vacuum gap 418. However, any number of sensors may be used. Alternatively, one or more sensors may be used. The exterior surface of each sensor membrane 412 is chemically functionalized to have an affinity for one or more specific, predetermined chemicals. The chemical functionalization can select for the presence of specific explosives or biohazard chemicals, but may also select for volatile organic compounds such as air pollutants, perfumes, and other aromas, as well as other chemicals in commercial and industrial applications. The sensors are designed for sensitivity to mass loading and stress loading by the adhered chemicals, and for matching into the electronic circuitry such as a Pierce oscillator or any other type of oscillator that is used to detect the shift in the property of the membrane. Due to the chemical functionalization of the membrane surface, the specific predetermined chemicals attach to the surface of the membrane 412 when they are present in the environment. Consequently, the operational characteristics (e.g., capacitance or resonant frequency) of the sensor will be altered.

The presence of the chemical in the environment can then be measured by detecting the alteration of the operating characteristics of the sensor. For example, an alteration in sensor characteristics can be detected by measuring the capacitance of the sensor, or by measuring the change in the resonant frequency of the functionalized membrane. Interconnects 420 through wafer 430 provide electrical contacts from the sensors 410 to a wafer 450 with electronics layer 460. The interconnects 420 are separated from the electronics 460 by an underfill 442 and solder balls 440. (While solder bumps are shown in this figure, contacts may be made between wafer 430 and wafer 450 by any means known in the art, e.g. with an anisotropic conducting film). The electronics layer 460 contains appropriate circuitry to drive and detect operational characteristics of the sensors. Additional signal processing electronics 470 may be attached to the sensor electronics to further process the signals and provide an indication of the presence of specific agents. The signal processing electronics measure and track the frequency output signals from the sensors to indicate the presence of agents.

Figure 4A:
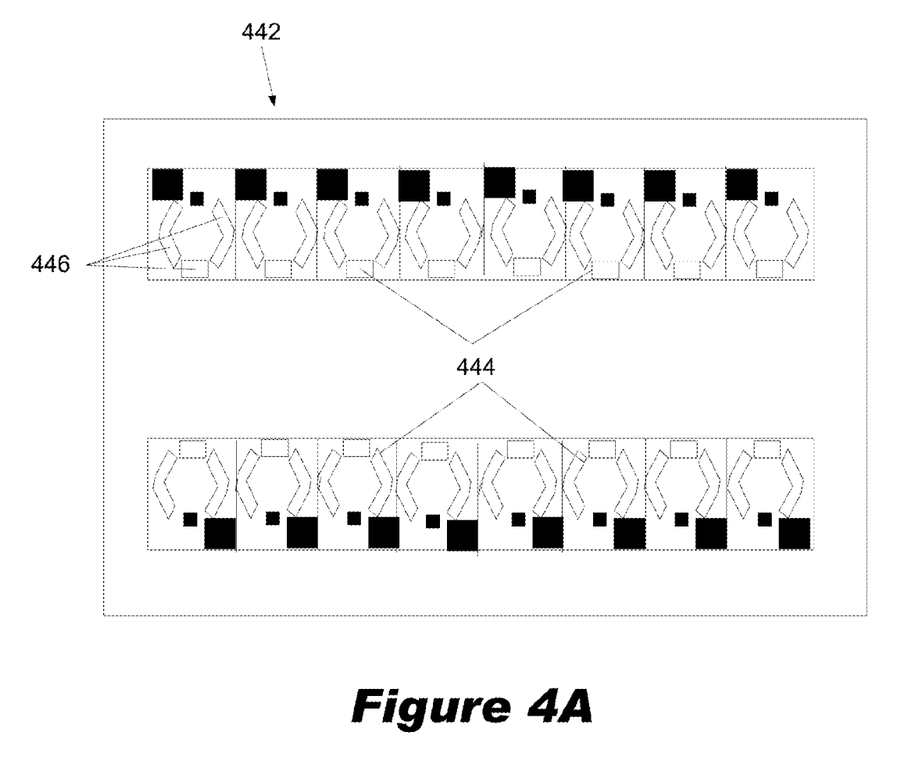
FIGS. 4A and 4B illustrate a top view of an example 16 channel capacitative micromachined ultrasound transducer device.
Figure 4B:
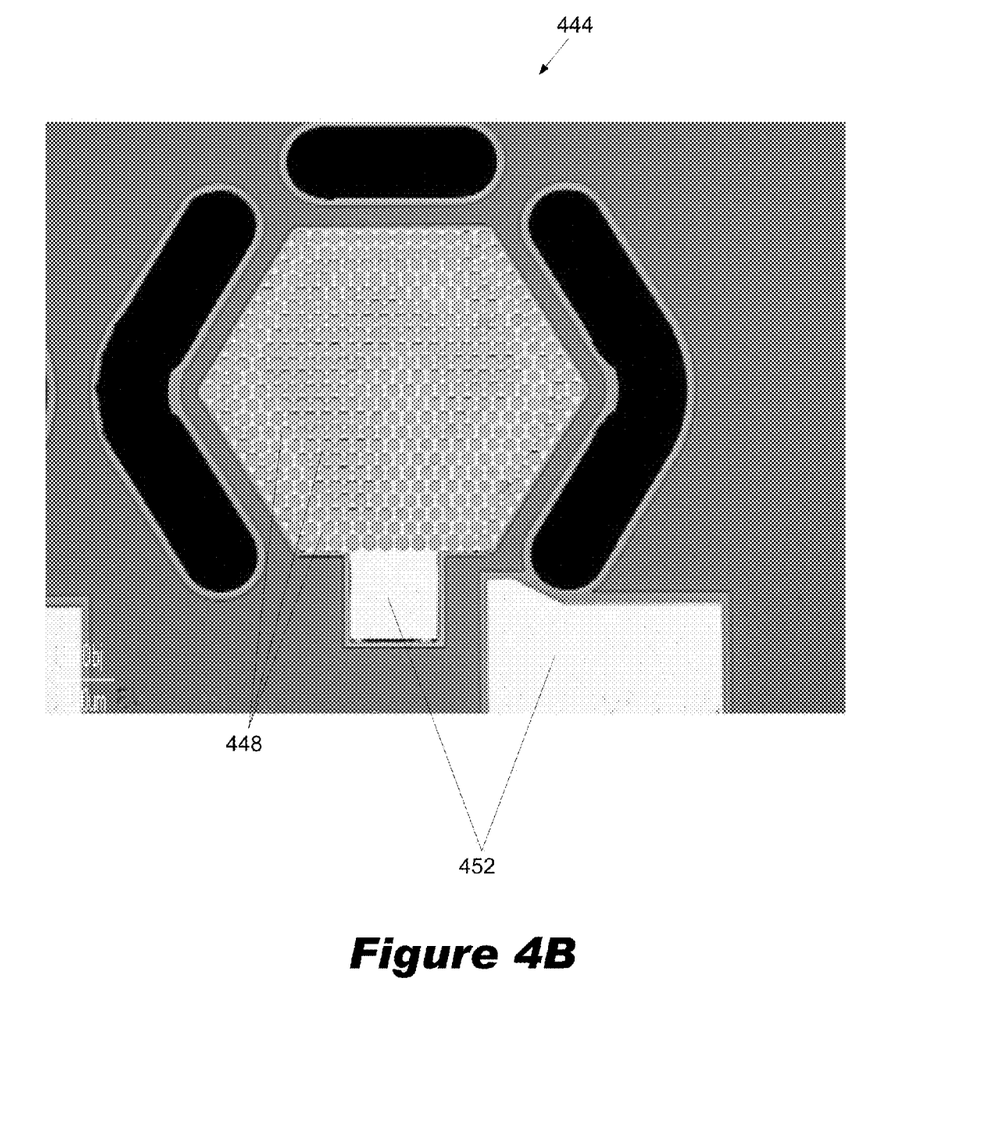

FIGS. 4A and 4B illustrate a top view of an example 16 channel capacitative micromachined ultrasound transducer device. Referring to FIG. 4A, the cMUT device 442 has 16 sensors 444. However, the number of sensors is not intended to be limiting as any number of sensors may be used. The resonant frequency of each sensor 444 can be dependent upon the mass of the membrane of the sensor 444. Further, the area of the sensor can be altered, such as with the addition of additional cavities 448. Each cavity may be formed with a specific dimension or have a diameter based upon the resonant frequency desired by the user.

FIG. 4B illustrates a top view of one sensor 444 illustrated in FIG. 4A. Each sensor 444 has a plurality of cavities 448. Each of the plurality of cavities 448 may have a diameter based upon the resonant frequency desired by the user. As illustrated, each sensor 444 has four hundred (400) cavities 448. However, the number of cavities is not intended to be limiting as any number of cavities may be used to achieve the desired resonant frequency. The plurality of cavities 448 are configured to communicate with the electrodes of the cMUT via wire bond pad areas 452, which may be attached to the first and second electrodes.

To mechanically isolate each sensor to prevent crosstalk between the sensors, vertical trenches 446 may be added between each sensor 444. The trenches 446 may be formed by any known etching process.

Chemical sensing is enabled by applying a layer of material to be analyzed to the membrane surface, which is reactive with analytes of interest in the material. The material may be of any form, such as a liquid, gas or solid. This "chemical functionalization" of the membrane can consist of a wide variety of materials ranging from non-selective polymers for gas adsorption to biologically active materials such as, but not limited to, proteins, or more specifically, antibodies, enzymes, and receptors, or nucleic acids, peptides, peptidomimetics, and peptoids.

The cMUT may be made with any of various known fabrication techniques including: silicon on insulator (SOI) bonding, sacrificial layer, and surface or bulk micromachining. The metal on the membrane is chosen to ensure the adhesion of the functionalizing chemical. The cMUT itself is designed for maximum sensitivity while taking into consideration its mechanical loading and electrical interfacing into the integrated (or non-integrated) electronic circuitry.

Sensors may be integrated with electronics in any of various known configurations including: flip chip bonding, elements constructed on top of electronics, or vice versa.

B. Liquid Sampling Using cMUT

Currently liquid sampling analysis is largely performed using passive microarray systems. The microarray system is typically a passive substrate upon which chemical functionalizations are applied in a grid pattern (the "array"). The array of functionalized spots can be composed of only a few sensors or many thousands, such as a passive 32,000-microarray.

Liquid samples are washed over the microarray and the materials in the sample bind to various sensors of the array depending upon interactions between the analytes and the functionalization chemistries of the membrane. The passive substrate typically does not contribute to the detection mechanism. The most common method of detection relies upon readout using a luminescent or fluorescent reader to scan for elements where a luminescent or fluorescent reporter has been "activated" due to the presence of binding of an analyte.

However, use of active microarray systems, such as the cMUT discussed above, may provide for a more accurate, time, and cost efficient analysis of the liquid samples. Active detection by the cMUT does not require the use of luminescent or fluorescent readers or reporters. The use of active detection can be read out electronically and the mass of the material that binds directly to the membrane may be determined electronically.

Figure 5:
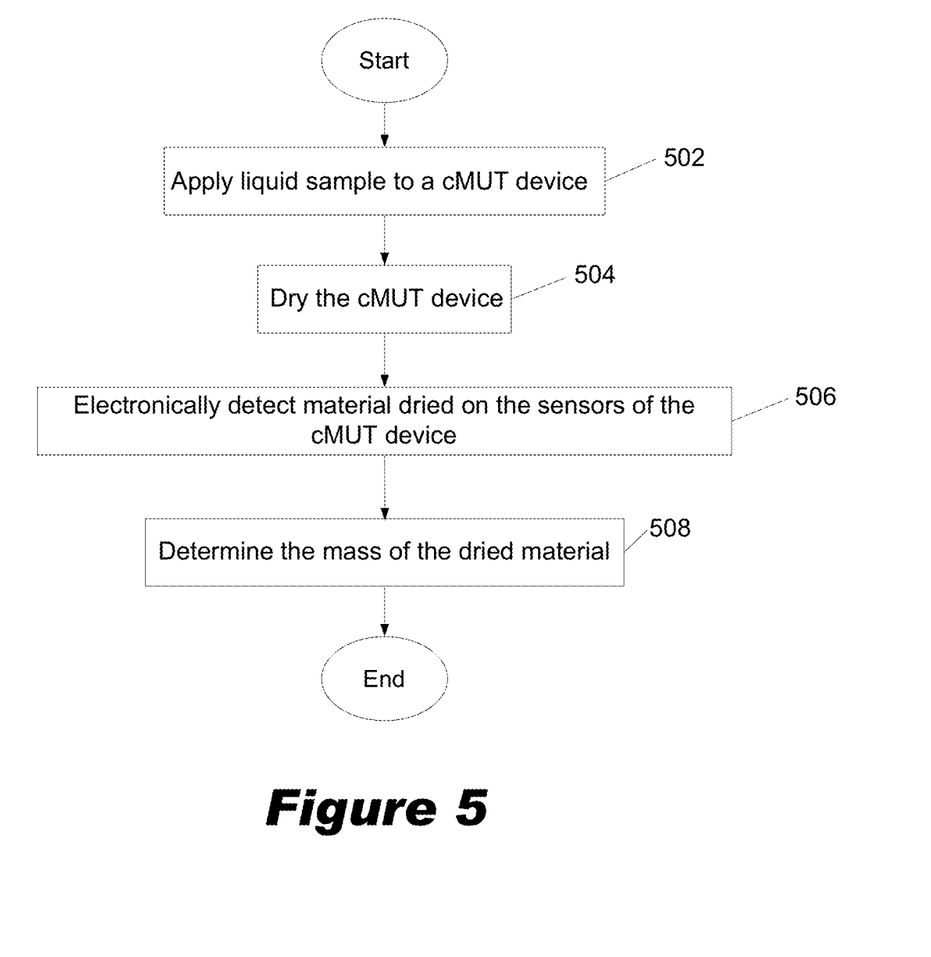
FIG. 5 illustrates a flow diagram of a method for analyzing liquids using a capacitative micromachined ultrasound transducer device.

FIG. 5 illustrates a flow diagram of a method for analyzing liquids using a capacitative micromachined ultrasound transducer device. In a washing step, a liquid sample may be applied to the cMUT device in 502. For example, the liquid sample to be analyzed may be introduced on to the surface of the cMUT device or the cMUT device can be temporarily submerged in the liquid for a predetermined period of time. For example, the cMUT device may be submerged in the liquid sample for between 1 second to 2 minutes.

The cMUT device is then dried at 504 prior to any measurements. The cMUT device may be dried using any known techniques, such as air drying, blowing heated air over the cMUT device, heating the cMUT device, and the like. Drying the cMUT device allows for a direct electronic detection of materials or agents that adhered or is bound to the membrane of each sensor on the cMUT device at 506. The electrical circuit of the sensor provides an output responsive to a mechanical resonance frequency responsive to the materials or agents that are bound to the functionalized membrane.

cMUT devices containing multiple sensors may have sensors whose membranes have different resonant frequencies. A membrane operating at low frequency yields a sensor more sensitive to stress on the membrane, whereas a membrane operating at high frequency gives a sensor that is more sensitive to mass loading. Combining various operating frequencies in one device thus provides a device with a greater versatility.

In such embodiments, electronics may be integrated with sensors, where multiple sensors are attached in parallel, and the sensors are operated at different frequencies so that one output line could be used. For this purpose, different sensors are built and operated at different frequencies. For example, a row of sensors can be made to resonate from 45 MHz to 55 MHz in 0.1 MHz intervals. Principles of dense wavelength division multiplexing (DWDM) may be used in such devices. In addition, the electronics may include temperature control circuitry such as a thermistor and heater resistor thermally coupled to the sensor or sensors and configured in a control loop for providing temperature stability to the sensors.

Each sensor of the cMUT device can be functionalized independently of the others. Having a cMUT device with thousands of sensors to make one cMUT device is very useful in establishing the electrical impedance of the device, and probably more importantly in reducing the number of false alarms as all the membranes in the device operates in parallel, and if one sensor were to give a false indication, all the other sensors force a correct decision. Having thousands of sensors, many of which are functionalized in the same fashion, can also be used to reduce the false alarm rates and provide a much more correct and stable measurement of the presence of compounds. Thus, if there is only a single sensor, or if multiple sensors are functionalized identically, the result is effectively a single detector.

If the sensors on the cMUT device are functionalized with multiple or different materials, the device becomes analogous to a microarray as commonly used in biological assays. Having sensors operating at multiple frequencies allow for electronic integration in transmitting information at different frequencies on the same channel, and in separating the influence of stress and mass loading on the shift in resonant frequency of a resonator.

The mass of the material dried on the sensor is determined at 508. For most microarray based assays, a labeling scheme is required to detect the binding or attachment of the analytes of interest to the array sensors. In many cases, luminescent or fluorescent readers or reporters are used and readout is achieved with an optical instrument.

However, since cMUTs provide an active substrate that is directly sensitive to the mass of the material that attaches or binds to each sensor, no such labeling scheme is required. This "label free" detection mode reduces the complexity of an assay and makes an assay possible for which a labeling scheme has not been developed. Additionally, this label free detection mode is more accurate since the role of labels is often questioned as a potential interference to the measurement of interest. Furthermore, since the readout system for the cMUT device is entirely electronic, the readout instrumentation may be much smaller and less expensive than many of the label based systems used today.

In another embodiment, a user may want to protect or encapsulate areas of the cMUT device from exposure to the liquid sample in the washing step and/or drying step discussed above. The areas may be protected by being coated or encapsulated with an inert encapsulant material such as a polymer or an epoxy. The encapsulant material can be applied, using any known application techniques, selectively to non-sensor areas by shielding the active sensor areas ("screening").

In another embodiment, the encapsulate material is applied to the entire cMUT device and then selectively removed from the sensor areas. This process is analogous to processes commonly used in semi-conductor production where photoresistive materials are selectively removed and etched via any known chemical procedures. For example, where the cMUT device is a microchip device is mounted on a printed circuit board or another active component, it may be desirable to also protect the circuit board or active component from exposure to the liquid sample. In this case, the encapsulating material may be applied to the microchip device and the surrounding component or circuit board. The result could be electronic or otherwise active components that are encapsulated in an inert material, similar to the process used in electronic fabrication known as "potting." Thus, the cMUT device, sensors, and associated electronics may be protected from exposure to liquids in the washing and drying steps by encapsulating or coating the areas with an inert material.

EXAMPLES

Examples are provided herein for exemplary purposes only and are not intended to be limiting in any way. For example, any microarray based assay method currently used today can be accomplished with the cMUT device described above.

Example 1

Early Stage Bacterial Growth Monitoring

Bacteria is introduced onto the sensor surface and grown with the sensor immersed in a growth medium. Any known growth mediums may be used. Periodic removal of the sensor for highly sensitive mass measurement will allow the growth rate of the bacteria colony to be monitored at very early time points. Additionally, the effects of treatments with various different materials such as, but not limited to, antimicrobials can be studied. In some cases, the growth medium may be applied to the sensor with the bacteria and be present during the measurement. The change in mass will occur due to metabolic uptake of materials from the atmosphere, such as oxygen, water vapor, and the like.

Example 2

Small Molecule Protein Interactions

The sensors of cMUT devices can be functionalized with a layer of protein including enzymes, antibodies, and receptors or peptides. Materials that will bind to the functionalized sensor surface can be introduced as described above in the washing and drying steps. The high sensitivity of the cMUT sensors make them particularly suitable for detecting the binding of small molecules of a few hundred daltons or less, a category of interaction that is of particular interest in drug discovery and development.

Example 3

Drug Screening

Drug screening is a broad application where many compounds are tested for interactions with specific materials of interest. Many existing screening technologies use microarray or microtiter well plate based assays. Most or all of these assays can be performed using the cMUT device described herein and most or all of these assays can be performed without label requirements. If used in conjunction with appropriate fluid handling systems (for example, robotics or microfluidics handling systems), the cMUT device sensors can also be used in High Throughput Screening applications.

Example 4

In vitro Diagnostics

Applications requiring identification of a particular pathogen or biomarker can be accomplished with appropriate functionalization of the cMUT sensor arrays, for example, an antibody panel can be fielded to detect a particular antigen associated with a specific disease state. In this example, cMUT sensors can be incorporated into instruments for In Vitro Diagnostics (IVD) such as microarray based assays, enzyme-linked immunosorbent assay (ELISA), and the like.

Example 5

Point of Care Diagnostics

The cMUT devices discussed herein and the corresponding readout instrumentation comprise an entirely electronic system, well suited to miniaturization. As such, the sensors may be used in conjunction with portable handheld held diagnostic instrumentation developed to address Point of Care (POC) needs such as those required for use in doctors' offices, hospitals, or home use by patients.

Example 6

Detection of Food Spoilage

Monitoring Foods For Bacteria or Other Contaminants

Because of the capability to miniaturize the system, such as is described in Example 5, the instrumentation could be developed into a handheld detection device allowing on-site monitoring of food products, such as freshness and contamination control in the meat processing industry prior to packaging and shipping.

Example 7

Measuring Molecular Interaction Under Flow

Using cMUT devices as discussed above, a device can be integrated into a microfluidics flow system allowing for molecular interaction under flow conditions thereby increasing sensitivity of the system by a factor of up to 50. Such a device may then be either removed from the flow-cartridge to allow endpoint measurements, or the liquid stream in the flow system may be diverted to allow subsequent in-channel drying of the sensor surface followed by read out.

Figure 6:
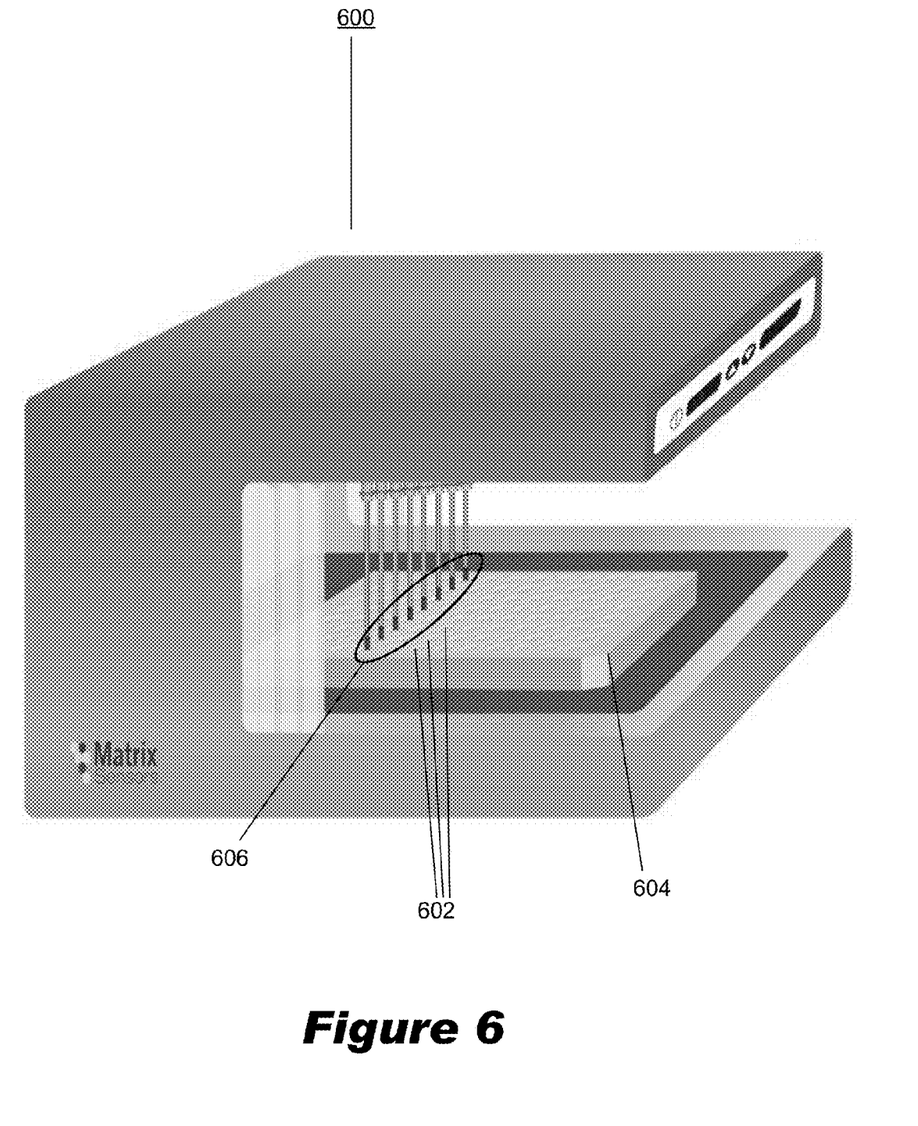
FIGS. 6 and 7 illustrate examples of apparatuses to carry out methods to analyze liquids using sensors that include a functionalized surface, by measuring a mechanical resonance frequency of the functionalized surface of each of the at least one sensor after a liquid has been applied and the surface dried.

Having described methods to analyze liquids using sensors that include a functionalized surface, by measuring a mechanical resonance frequency of the functionalized surface of each of the at least one sensor after a liquid has been applied and the surface dried, we now describe some examples of apparatuses that may be utilized to carry out such methods. For example, FIG. 6 illustrates a reader apparatus 600 that includes a well plate 604 having wells 602 to contain one or more liquids to analyze. Probes 608 each include, at a tip region thereof, at least one sensor of a type as described above. In use, the probes may be dipped into the liquid-containing wells 602 and then lifted out and allowed to dry. Further, in practice, any number of probes may be utilized, including a single probe.

The reader apparatus 600 includes an integrated or external microprocessor programmed to carry out the steps of the method such as causing the probes to be dipped into the wells 602 to cause the liquid to be applied to the functionalized surface of the sensors, causing the probes to be withdrawn from the wells 602 so that the functionalized surface is dried, and activating sensor electronics to cause the mechanical resonance frequencies of the dried surfaces to be measured and, based thereon, to determine whether the liquids contain one or more particular agents, all as described in detail above. Results may be provided to a display housed in the reader apparatus 600 itself or communicated to another apparatus such as using a computer-to-computer interface.

Figure 7:
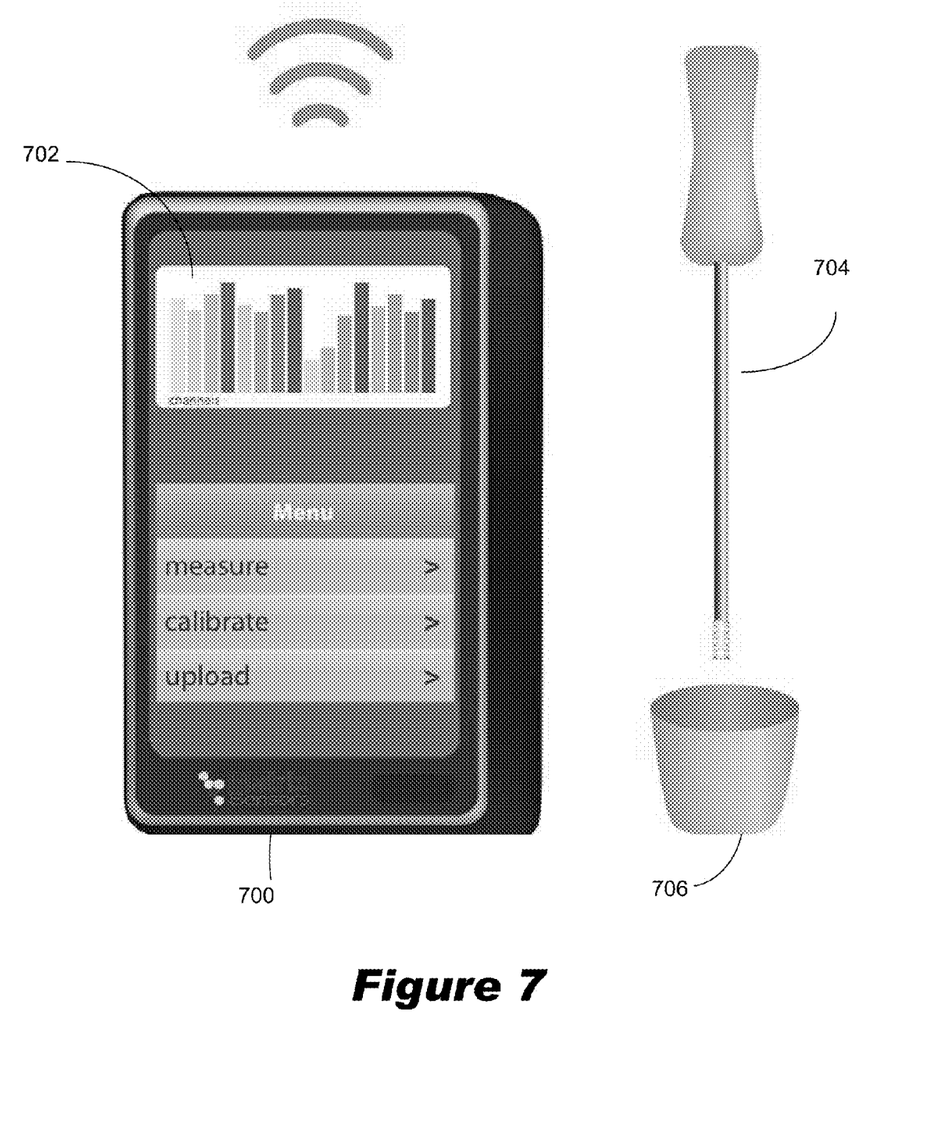

FIG. 7 illustrates a portable reader apparatus 700 that may utilized with a portable probe 704. The probe 704, like the probes 608, includes at a tip region at least one sensor of the type described above. In use, the probe may be manually dipped into a vessel 706 that contains a liquid to be analyzed, to cause the liquid to be applied to the functionalized surface of the sensors. The reader apparatus 700 may house an environmental chamber having an environment (e.g., slightly heated) that causes the functionalized surface to dry. Also, electronics are housed within the reader apparatus for measuring the mechanical resonance frequencies of the sensors of the probe 704. A display 702 may be provided to convey results to a user. The results may be raw data or may be processed to be more meaningful to a lay user. As with the apparatus 600, results may also be uploaded to another system such as using a computer-to-computer interface, e.g., in a wired or wireless manner.

Both the apparatus 600 and the apparatus 700 generally operate under control of a microprocessor executing computer program instructions. The step of providing results to a user may be accomplished, for example, by applying a formula from which a mass of an agent bound to the functionalized surface of a sensor may be determined based on the measured mechanical resonance frequency of the sensor surface. In other examples, a lookup table may be utilized.

While embodiments and applications of this invention have been shown and described, it would be apparent to those skilled in the art having the benefit of this disclosure that many more modifications than mentioned above are possible without departing from the inventive concepts herein.

What is claimed is:

1. A method for analyzing liquid samples, comprising:
applying a liquid to immerse a capacitive micromachined ultrasound transducer (cMUT) device having at least one sensor, each of the at least one sensor including:
a functionalized surface functionalized with one from the group consisting of: a functionalized surface including a layer of protein for detecting small molecule protein interactions, a surface functionalized for drug screening, a surface functionalized for in vitro diagnostics, a surface functionalized for point-of-care diagnostics, and a surface functionalized for detecting food spoilage;
an electrical oscillator circuit that, in combination with a resonant electrical input impedance of the sensor, establishes a resonant circuit; and
encapsulation to protect electronics portions of the cMUT device from the liquid in regions exterior to the functionalized surface;
drying each of the at least one sensor;
after the drying step, measuring, using a separate electronics unit housed within an apparatus external to the cMUT device, a resonant frequency of the electrical oscillator circuit of each of the at least one sensor; and
determining, via the separate electronics unit, whether the liquid includes a particular agent, based on a result of the measuring step;
wherein the electronics unit for measuring resonant frequencies and determining whether the liquid includes the particular agent is a separate unit from the cMUT device and is protected from contact with the liquid.

2. A method for analyzing liquid samples for small molecule protein interactions, comprising:
applying a liquid to immerse a capacitive micromachined ultrasound transducer (cMUT) device having at least one sensor, each of the at least one sensor including:
a functionalized surface functionalized with a layer of protein including one of enzymes, antibodies, receptors, and peptides;
an electrical oscillator circuit that, in combination with a resonant electrical input impedance of the sensor, establishes a resonant circuit; and
encapsulation to protect electronics portions of the cMUT device from the liquid in regions exterior to the functionalized surface;
drying each of the at least one sensor;
after the drying step, measuring, using a separate electronics unit housed within an apparatus external to the cMUT device, a resonant frequency of the electrical oscillator circuit of each of the at least one sensor; and
determining, via the separate electronics unit, whether the liquid includes a particular agent, based on a result of the measuring step;
wherein the electronics unit for measuring resonant frequencies and determining whether the liquid includes the particular agent is a separate unit from the cMUT device and is protected from contact with the liquid.

3. A method for analyzing liquid samples for drug screening, comprising:

applying a liquid to immerse a capacitive micromachined ultrasound transducer (cMUT) device having at least one sensor, each of the at least one sensor including:
  a functionalized surface selected to be responsive to materials to be detected in drug screening;
  an electrical oscillator circuit that, in combination with a resonant electrical input impedance of the sensor, establishes a resonant circuit; and
  encapsulation to protect electronics portions of the cMUT device from the liquid in regions exterior to the functionalized surface;
drying each of the at least one sensor;
after the drying step, measuring, using a separate electronics unit housed within an apparatus external to the cMUT device, a resonant frequency of the electrical oscillator circuit of each of the at least one sensor; and
determining, via the separate electronics unit, whether the liquid includes a particular agent, based on a result of the measuring step, wherein presence of the particular agent provides information for drug screening;
  wherein the electronics unit for measuring resonant frequencies and determining whether the liquid includes the particular agent is a separate unit from the cMUT device and is protected from contact with the liquid.

4. A method for analyzing liquid samples for in vitro diagnostics, comprising:
  applying a liquid to immerse a capacitive micromachined ultrasound transducer (cMUT) device having at least one sensor, each of the at least one sensor including:
    a functionalized surface selected to detect a particular antigen;
    an electrical oscillator circuit that, in combination with a resonant electrical input impedance of the sensor, establishes a resonant circuit; and
    encapsulation to protect electronics portions of the cMUT device from the liquid in regions exterior to the functionalized surface;
  drying each of the at least one sensor;
  after the drying step, measuring, using a separate electronics unit housed within an apparatus external to the cMUT device, a resonant frequency of the electrical oscillator circuit of each of the at least one sensor; and
  determining, via the separate electronics unit, whether the liquid includes a particular agent, based on a result of the measuring step, wherein presence of the particular agent provides information for determining the presence of the particular antigen;
    wherein the electronics unit for measuring resonant frequencies and determining whether the liquid includes the particular agent is a separate unit from the cMUT device and is protected from contact with the liquid.

5. A method for analyzing liquid samples for point-of-care diagnostics, comprising:
  applying a liquid to immerse a capacitive micromachined ultrasound transducer (cMUT) device having at least one sensor, each of the at least one sensor including:
    a functionalized surface;
    an electrical oscillator circuit that, in combination with a resonant electrical input impedance of the sensor, establishes a resonant circuit; and
    encapsulation to protect electronics portions of the cMUT device from the liquid in regions exterior to the functionalized surface;
  drying each of the at least one sensor;
  after the drying step, measuring, using a separate electronics unit housed within a portable handheld diagnostic device external to the cMUT device, a resonant frequency of the electrical oscillator circuit of each of the at least one sensor; and
  determining, via the separate electronics unit, whether the liquid includes a particular agent, based on a result of the measuring step;
    wherein the electronics unit for measuring resonant frequencies and determining whether the liquid includes a particular agent is a separate unit from the cMUT device and is protected from contact with the liquid.

6. A method for detecting food spoilage using a handheld unit, comprising:
  applying a liquid to immerse a capacitive micromachined ultrasound transducer (cMUT) device having at least one sensor, each of the at least one sensor including:
    a functionalized surface selected to be responsive to materials indicative of food contamination;
    an electrical oscillator circuit that, in combination with a resonant electrical input impedance of the sensor, establishes a resonant circuit; and
    encapsulation to protect electronics portions of the cMUT device from the liquid in regions exterior to the functionalized surface;
  drying each of the at least one sensor;
  after the drying step, measuring, using a separate electronics unit housed within a handheld detection apparatus external to the cMUT device, a resonant frequency of the electrical oscillator circuit of each of the at least one sensor; and
  determining, via the separate electronics unit, whether the liquid includes a particular agent, based on a result of the measuring step;
    wherein the electronics unit for measuring resonant frequencies and determining whether the liquid includes the particular agent is a separate unit from the cMUT device and is protected from contact with the liquid.

* * * * *